US008862238B2

(12) United States Patent
Rahimi et al.

(10) Patent No.: US 8,862,238 B2
(45) Date of Patent: Oct. 14, 2014

(54) SYSTEM AND METHOD FOR MANAGING PAIN

(71) Applicant: Thimble Bioelectronics, Inc., Santa Clara, CA (US)

(72) Inventors: Shaun Ramin Rahimi, Santa Clara, CA (US); Earl Corban Vickers, San Jose, CA (US)

(73) Assignee: Thimble Bioelectronics, Inc., Santa Clara, CA (US)

( * ) Notice: Subject to any disclaimer, the term of this patent is extended or adjusted under 35 U.S.C. 154(b) by 0 days.

(21) Appl. No.: 13/951,764

(22) Filed: Jul. 26, 2013

(65) Prior Publication Data

US 2014/0031895 A1 Jan. 30, 2014

Related U.S. Application Data

(60) Provisional application No. 61/676,908, filed on Jul. 28, 2012.

(51) Int. Cl.
*A61N 1/00* (2006.01)
*A61N 1/36* (2006.01)

(52) U.S. Cl.
CPC ............. *A61N 1/36071* (2013.01); *A61N 1/36* (2013.01)
USPC .......................................................... 607/46

(58) Field of Classification Search
USPC .......................................................... 607/46
See application file for complete search history.

(56) References Cited

U.S. PATENT DOCUMENTS

| 2012/0089045 | A1* | 4/2012 | Seidl et al. ................... 600/547 |
| 2012/0116478 | A1* | 5/2012 | Buhlmann et al. .............. 607/48 |
| 2014/0005759 | A1* | 1/2014 | Fahey et al. ..................... 607/99 |
| 2014/0012157 | A1* | 1/2014 | Gilhuly, Terence ........... 600/554 |
| 2014/0046423 | A1* | 2/2014 | Rajguru et al. ............... 607/144 |

OTHER PUBLICATIONS

Malesevic et al., "Classification of muscle twitch response using ANN: Application in multi-pad electrode optimization," IEEE 2010.
Malesevic et al., "INTFES: A multi-pad electrode system for selective transcutaneous electrical muscle stimulation," date unknown.
Malesevic et al., "Muscle twitch responses for shaping the multi-pad electrode for functional electrical stimulation," IEEE Journal of Automatic Control, University of Belgrade, vol. 20:53-58, 2010.

(Continued)

*Primary Examiner* — Robert N Wieland
(74) *Attorney, Agent, or Firm* — Jeffrey Schox; Ivan Wong

(57) ABSTRACT

A system and method for managing pain, configured to be worn by a patient, comprising an electrode array comprising a first electrode and a second electrode for providing a TENS treatment to the patient; a connector configured to couple at least one of the first electrode and the second electrode to an electronics subsystem; a muscle twitch sensor subsystem configured to detect a muscle twitch profile induced by the electrode array at the patient; and an electronics subsystem comprising a power module configured to power the system, a pulse generator coupled to the electrode array and configured to transmit the TENS treatment, and a control module configured to receive an input, from the muscle twitch sensor subsystem, characterizing the muscle twitch profile, wherein the electronics subsystem is configured to modulate a parameter of the TENS treatment based upon the input, until a threshold is satisfied.

20 Claims, 9 Drawing Sheets

(56) References Cited

OTHER PUBLICATIONS

Biggs et al., "A Comparison of the Hypoalgesic Effects of Transcutaneous Electrical Nerve Stimulation (TENS) and Non-invasive Interactive Neurostimulation (InterX®) on Experimentally Induced Blunt Pressure Pain Using Healthy Human Volunteers", Neuromodulation 2012; 15: 93-99.

Jordan Kahn, "Hands on with 'i-Massager' iPhone-controlled electrical nerve stimulation and other iOS massage accessories", 9TO5Mac, http://9to5mac.com/2013/01/09/hands-on-with-i-massager-iphone-controlled-electrical-nerve-stimulation-and-other-ios-massage-accessories/ Jan. 9, 2013.

Kolen et al., "Effects of spatially targeted transcutaneous electrical nerve stimulation using an electrode array that measures skin resistance on pain and mobility in patients with osteoarthritis in the knee: A randomized controlled trial." J. Pain, 153 (2012) 373-381, doi:10.1016/j.pain.2011.10.033.

Sauter et al., "Current threshold for nerve stimulation depends on electrical impedance of the tissue: a study of ultrasound-guided electrical nerve stimulation of the median nerve." Anesth Analg. Apr. 2009;108(4):1338-43. doi: 10.1213/ane.0b013e3181957d84.

\* cited by examiner

SYSTEM AND METHOD FOR MANAGING PAIN

CROSS-REFERENCE TO RELATED APPLICATIONS

This application claims the benefit of U.S. Provisional Application Ser. No. 61/676,908 filed 28 Jul. 2012, which is incorporated in its entirety herein by this reference.

TECHNICAL FIELD

This invention relates generally to the pain management device field, and more specifically to a new and useful system and method for managing pain.

BACKGROUND

Transcutaneous electrical nerve stimulation (TENS) is increasingly becoming a medically accepted alternative to pharmaceutical pain treatments. TENS was originally introduced for treating chronic back pain, and then later extended to treat other types of pain as well; however, the mechanism by which TENS treatment methods reduce pain are not fully understood. Current theories suggest that TENS activates central nervous system opioid receptors, and/or increases levels of endorphins. However, receptor activation by TENS is also not well-understood and complex, and the type(s) of opioid receptor(s) activated and the extent of activation can vary depending upon variations in TENS stimulation parameters. In addition to the lack of understanding regarding TENS mechanisms for managing pain, current TENS treatments exhibit susceptibility to patient and body region variability, require substantial manual adjustment of treatment parameters, are motion-limiting, lack portability, and/or are difficult to use.

There is thus a need in the pain management device field to create a new and useful system for managing pain. This invention provides such a new and useful system and method.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. System

Figure 1A:
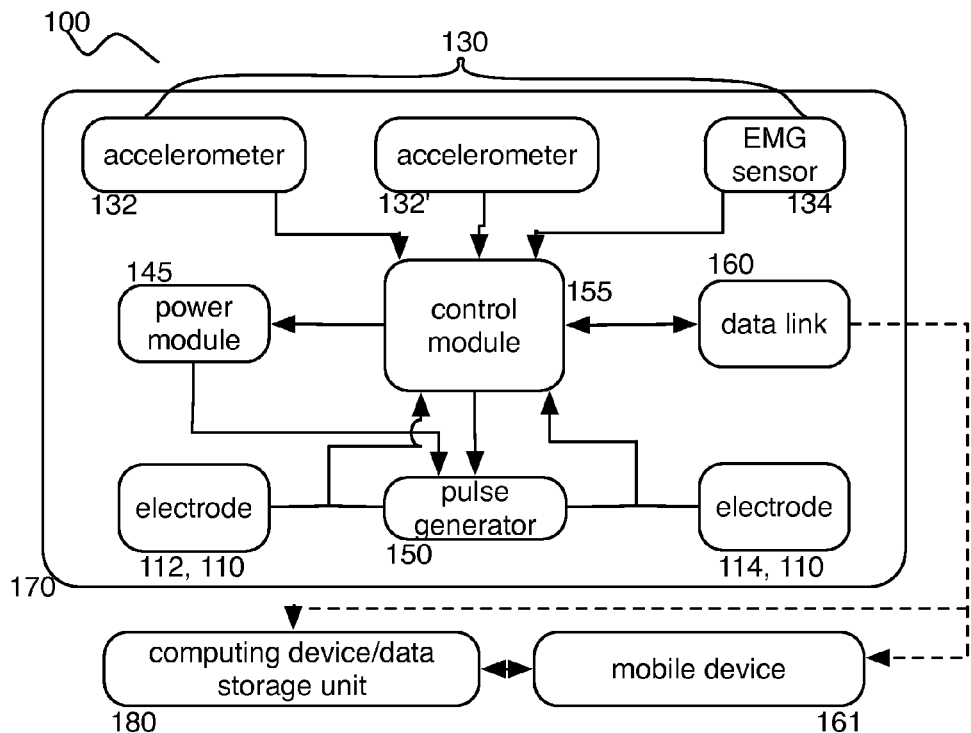
FIGS. 1A and 1B depict an embodiment of a system for managing pain of a patient.
Figure 1B:
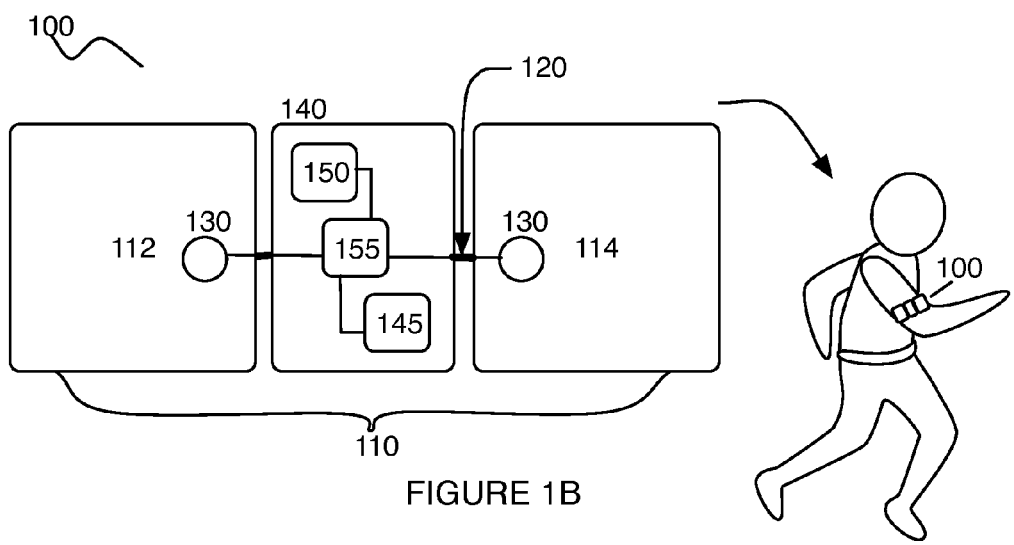

As shown in FIGS. 1A and 1B, an embodiment of a system 100 for managing pain of a patient comprises an electrode array 110 comprising a first electrode 112 and a second electrode 114 for providing a TENS treatment; a muscle twitch sensor subsystem 130 configured to detect a muscle twitch profile induced by the electrode array 110; and an electronics subsystem 140 comprising a power module 145, a pulse generator 150, and a control module 155 configured to receive an input from the muscle twitch sensor subsystem 130 characterizing the muscle twitch profile, wherein the electronics subsystem is configured to modulate a parameter of the TENS treatment based upon the input, until an adjusted muscle twitch profile detected at the muscle twitch sensor subsystem 130 satisfies a threshold. In some embodiments, the system 100 can further comprise a connector 120 configured to couple the first electrode 112 and the second electrode 114 to the electronics subsystem 140; a data link 160 configured to transmit outputs from the system 100 to an external module and/or to receive inputs from an external module. The system 100 can also further comprise a housing 170 configured to house elements of the system 100 and to protect elements of the system 100 over its lifetime of usage.

The system 100 functions to provide a self-regulating, adaptable, and automated pain management tool for the patient, that can be worn by the patient as the patient performs activities (e.g., exercising, playing sports, working, resting) in his or her daily life. Furthermore, the system 100 preferably functions to manage a patient's musculoskeletal pain associated with, for example, sore or aching muscles of the lower back, arms or legs due to strain from exercise, work activities, or injury. The system 100 is preferably configured to reduce a patient's pain level, but can alternatively be used to prevent a patient from entering a state of pain, be used to adjust a patient's pain tolerance, and/or be used in any other suitable manner to adjust a patient's experience or sensation of pain. Additionally, the system 100 preferably functions to manage a patient's chronic pain symptoms; however, the system 100 can additionally or alternatively function to manage a patient's acute pain symptoms.

Preferably, the system 100 is configured to be worn by the patient outside of a clinical (e.g., hospital) or research (e.g., laboratory) setting, such that the patient can be in a non-contrived environment as he or she is receiving the TENS treatment. Furthermore, elements of the system 100 can be reusable or disposable, or the entire system 100 can be configured to be disposable. In one specific example, the system 100 is a unitized system 100 that adheres to the patient (thus not compelling the patient to hold any part of the system 100 by hand), has a low, bandage-like profile that conforms to the patient, and is configured to deliver TENS treatment in an automatically modulated manner to a patient who is substantially removed from clinical/research staff. Alternatively, the system 100 can be substantially non-portable, non-wearable, and/or intended for use in a clinical or research setting.

1.1 Electrode Array

The electrode array 110 functions to deliver a TENS treatment to the patient, wherein parameters of the TENS treatment are facilitated using the electronics subsystem 140. Preferably, the electrode array 110 comprises a first electrode 112 and a second electrode 114, but can additionally comprise any suitable number of electrodes for providing a TENS treatment to the patient. The positions of the electrodes in the electrode array 110 are preferably constrained relative to each other (e.g., by a connector, as described below), while still allowing individual electrodes of the electrode array 110 to be manipulated relative to each other with at least one degree of freedom. In one variation, the electrodes of the electrode array 110 are arranged along a single axis in a first configuration, but can be displaced along the axis in order to conform to a curved surface of the patient's body. In other variations, the electrodes of the electrode array can be arranged along any number of axes and can be manipulated relative to the axes in any other suitable manner. Preferably, the electrode array 110 is configured to interface with the patient at a site (e.g., body region) proximal to where the patient is experiencing pain (e.g., configured to straddle a painful site). Thus, the electrode array no is preferably versatile and in some examples, can be positioned and/or repositioned proximal to facial muscles (e.g., to treat trigeminal neuralgia), proximal to the pectoralis muscles (e.g., to treat thalamic pain or angina), proximal to the pelvic muscles (e.g., to treat dysmenorrhoea), proximal to the knee joint (e.g., to treat arthritic pain), proximal to the rotator cuff muscles to treat shoulder pain, and/or proximal to the hamstring muscles (e.g., to treat pain associated with sciatica). However, the electrode array no can alternatively be positioned at any other suitable body region of the patient, for delivering the TENS treatment to the patient. For example, the electrode array no can be configured to be positioned at a body region substantially removed from the site at which the patient is experiencing pain (e.g., at a contralateral limb for a patient who is experiencing limb pain, at a remote site to treat phantom limb pain, near the spinal cord at an origin site of pain), such that the treatment is actualized by a remote stimulation mechanism. In another alternative variation, the electrode array no can be configured to discourage placement at some body regions of the patient, such as by way of geometric configurations and/or shapes of the electrodes of the electrode array no.

Figure 2:
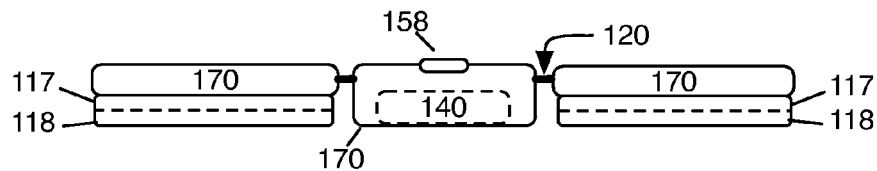
FIG. 2 depicts an embodiment of a system for managing pain of a patient.

The first electrode 112 of the electrode array no functions to serve as a cathode electrode, which, in cooperation with the second electrode 114, is configured to provide transcutaneous electrical nerve stimulation. The first electrode 112 can additionally or alternatively function as an anode electrode in alternative variations, and in one variation, functions as both a cathode and an anode in an alternating manner during provision of a biphasic signal as the TENS treatment. The first electrode 112 is preferably disposable in a modular variation of the system 100, but can alternatively be reusable in other variations. As shown in FIG. 2, the first electrode 112 preferably comprises a conducting region 117, wherein the conducting region 117 is composed of at least one conducting material. In some variations, the conducting region 117 is composed of a conducting hydrogel, a non-hydrogel polymeric material, a metal or metal alloy, a carbon or silicon-based material, or a composite of any of the various materials. The conducting region 117 can be adhesive or can be coupled to an adhesive layer 118, such that the first electrode can be semi-permanently or reversibly affixed to a treatment site at the patient. Alternatively, the first electrode 112 can be affixed to the patient by any other suitable means, such as a snap-on button, a clip mechanism, a slip-on sheath, or a strap. Furthermore, the material(s) used in the first electrode 112 are preferably biocompatible and comply with safety standards (e.g., ANSI/AAMI/ISO 10993-1:2003, "Biological evaluation of medical devices—Part 1, Evaluation and testing within a risk management process"). The first electrode 112 preferably has a rectangular profile and a thin transverse cross section, as shown in FIGS. 1B and 2, to facilitate uniformity of electrical stimulus transmission between electrodes and to reduce bulk. However, the first electrode 112 can alternatively have any other suitable geometric profile (e.g., polygonal, triangular, circular, ellipsoidal, amorphous, curvilinear) and/or thickness. Furthermore, to facilitate disposability and/or modularity of the system 100, the first electrode 112 can reversibly couple to the system 100 using any suitable means, such as a snap-on button, clip mechanism, slip-on sheath or sleeve, and/or any other suitable mechanism.

The second electrode 114 of the electrode array 110 functions to serve as an anode electrode to the first electrode 112, for provision of transcutaneous electrical nerve stimulation. In a similar manner to the first electrode 112, the second electrode 114 can alternatively function as a cathode electrode, and in one variation functions as both a cathode and an anode in an alternating manner during provision of a biphasic signal as the TENS treatment. The second electrode 114 is preferably identical to the first electrode 112 in form and composition, as described above, in order to facilitate uniformity of the electrical characteristics of the first electrode 112 and the second electrode 114. However, the second electrode 114 can alternatively be different from the first electrode 112 in form, in order to increase the number of positions at which the electrode array no can be placed, and can additionally or alternatively be different from the first electrode 112 in composition, in order to provide non-uniform electrical characteristics between the first and the second electrodes 112, 114.

Figure 3:
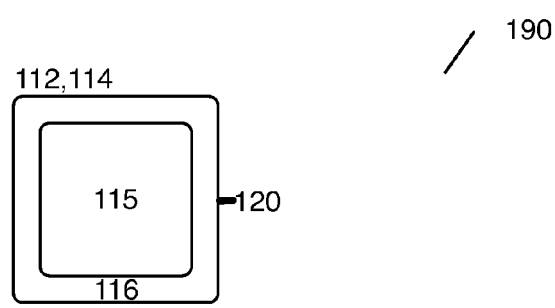
FIG. 3 depicts a variation of an electrode of an embodiment of a system for managing pain of a patient.

In some variations, as shown in FIG. 3, the first electrode 112 and the second electrode 114 each comprise a first surface area 115 and a second surface area 116 configured to enable detection of resistance and/or impedance changes resulting from delamination or breaching of an interface between an electrode 112, 114 and the patient. In order to enable detection of resistance and/or impedance changes, the first surface area 115 and the second surface area 116 can have different resistances produced by different geometric features, by different materials, or in any other suitable manner. In one variation, the first surface area 115 and the second surface area 116 are different shapes (e.g., the first surface area is rectangular and the second surface area is ellipsoidal), and in another variation, the first and the second surface areas 115, 116 are the same shape, but have different total areas. As such, when the first and the second electrodes 112, 114 form a complete interface with the patient's skin, a nominal resistance can be detected, which indicates that delamination or breaching of the electrode-patient interface has not occurred. However, when contact between the surface areas 115, 116 of an electrode 112, 114 and the patient's skin is reduced due to delamination or breaching, a change (e.g., increase due to reduced area) in resistance or impedance can be detected and used, for example, to modulate the TENS treatment.

In a specific example, the first electrode 112 and the second electrode 114 are each disposable electrodes that have a life span of at least one week before disposal, have a square profile (2 inches×2 inches) with rounded edges, and have thicknesses of less than 0.25 inches. The electrodes 112, 114 in the specific example are composed of a silicate hydrogel that is conducting, and that can be reversibly affixed to the patient prior to disposal. The electrodes 112, 114 also comprise first and second surface areas 115, 116, wherein the first surface area 115 is approximately 50% of the total surface area of a given electrode 112, 114, and the second surface area 116 is approximately 50% of the total surface area of a given electrode 112, 114. Thus, the first surface area 115 and the second surface area 116 are each approximately 2 inches square in area, but in other variations of the specific example, can comprise any other suitable portion of one of the first electrode 112 and the second electrode 114.

1.2 Connector

The connector 120 is configured to extend between electrodes of the electrode array 110, and functions to couple the first electrode 112 and the second electrode 114 to an electronics subsystem 140, as described below. The connector 120 also preferably mechanically couples the first electrode 112 to the second electrode 114 by way of a mechanically robust coupler that protects the electrical connection(s) against mechanical failure. The connector 120 preferably limits the separation between the first and the second electrode 112, 114 while allowing manipulation of each electrode individually, such that the first and the second electrodes 112, 114 can be placed at any suitable location (e.g., planar or non-planar surface) to provide the TENS treatment. The connector 120 thus preferably allows adjustability of the positions of the first and the second electrodes 112, 114 along an axis, while allowing a position of either the first or the second electrode 112, 114 to deviate from the axis by translation and/or rotation with any suitable number of degrees of freedom (e.g., to allow the electrodes to be placed about a curved portion of the surface of the patient). In some variations, the connector 120 can comprise a strain gage or other suitable deformation or position sensor, such that deformation of the connector 120 and/or the positions of the electrodes of the electrode array 110 can be used to indicate placement of the electrodes 112, 114 on the patient's body, as another input to modulate the TENS treatment provided by the system 100.

Figure 4A:
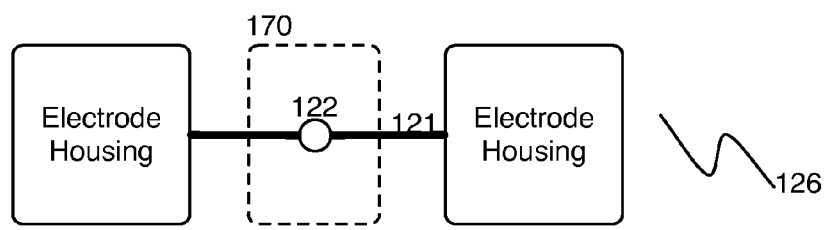
FIGS. 4A and 4B depict configurations of an embodiment of a system for managing pain of a patient.
Figure 4B:
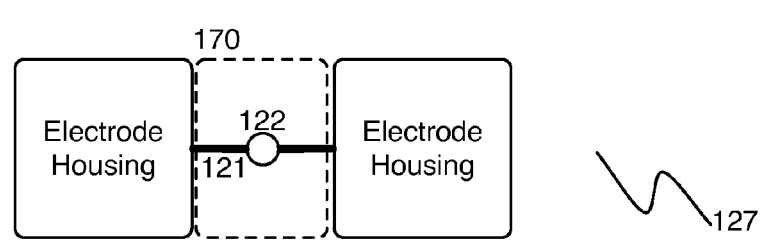

In a first variation, the connector 120 can be a retractable cable 121, as shown in FIGS. 4A and 4B, wherein the retractable cable 121 couples to the first and the second electrodes 112, 114 and to the electronics subsystem 140 to facilitate transmission of electrical stimulation. The retractable cable 121 in the first variation is preferably flexible, thus providing extension and/or rotation to facilitate versatility in position of the electrodes 112, 114. The retractable cable 121 provides the retraction by a retraction module 122, and in a specific example, the retraction module 122 is a pinwheel 122 that allows the retractable cable 121 to maintain a certain extension length in a first configuration 126, and allows the extension length to be retracted or released in a second configuration 127. The pinwheel 122 in the specific example is positioned midway along an axis between the first and the second electrodes 112, 114, such that equilateral extension of the electrodes 112, 114 can be provided by the retractable cable 121 and the pinwheel 122. In the specific example, the retractable cable 121 has a maximum extension of 8 inches, but in alternatives to the specific example, the retractable cable 121 can provide any suitable extension length. In the specific example, the retraction module 122 can further comprise an actuation system (e.g., electronic motor, pneumatic motor) that provides powered action of the connector and displacement of the electrodes 112, 114. In alternatives to the first variation, the retraction module 122 and/or the retractable cable 121 can be configured to provide non-equilateral extension of electrodes 112, 114, and furthermore, the alternatives to the first variation can comprise any suitable number of retractable cables 121 and/or retraction modules 122.

Figure 5A:
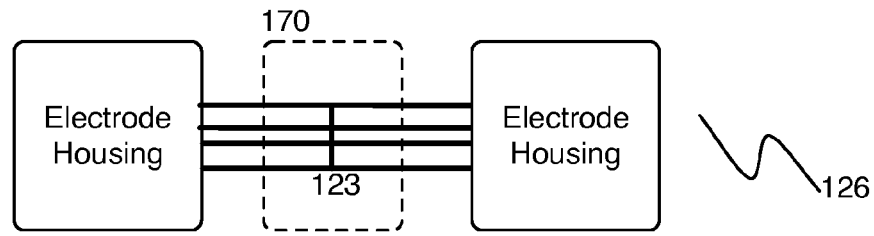
FIGS. 5A and 5B depict configurations of an embodiment of a system for managing pain of a patient.
Figure 5B:
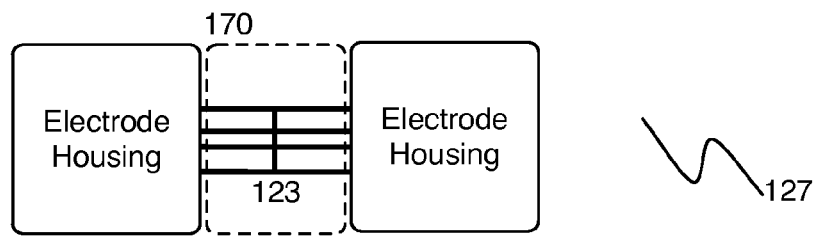

In a second variation, as shown in FIGS. 5A and 5B, the connector 120 can be a flexible sliding track 123 that allows the first and the second electrodes 112, 114 to be displaced from each other. The flexible sliding track 123 in the second variation provides a guide along which the first and the second electrodes 112, 114 can be displaced from one another, while flexion and torsion of the flexible sliding track 123 provides displacement away from a linear axis and rotation of the first electrode 112 and/or the second electrode 114. The flexible sliding track 123 can comprise a set of stopping positions, such that a displacement between the first and the second electrodes 112, 114 can be maintained by a subset of the stopping positions, and the displacement can be further adjusted by adjusting the flexible sliding track 123 along the stopping positions. Displacement along the flexible sliding track 123 can, however, be stopped using any other suitable mechanism. The flexible sliding track 123 is preferably flexible in an elastic manner, such that removal of the first and the second electrodes 112, 114 returns the flexible sliding track 123 to an undeformed configuration; however, the flexible sliding track 123 can additionally or alternatively be flexible in a non-elastic manner, such that a deformation of the flexible sliding track 123 is maintained until the flexible sliding track 123 is further deformed.

In other variations, the connector 120 can comprise any suitable combination of the first and the second variations, and can additionally or alternatively comprise any other suitable mechanism for enabling versatile displacement of the first and the second electrodes 112, 114 relative to one another, while still providing a mechanical connection between the first and the second electrodes 112, 114, and/or an electrical connection from the first electrode 112 and the second electrode 114 to the electronics subsystem 140.

a muscle twitch sensor subsystem configured to measure a set of muscle twitches induced by the electrode array at the patient, thereby yielding a measured muscle twitch signal characterized by a set of measured muscle twitch values

1.3 Muscle Twitch Sensor Subsystem

The muscle twitch sensor subsystem 130 is configured to interface with the patient while the patient is experiencing the TENS treatment, and functions to detect a muscle twitch profile comprising any muscle movements, vibrations, contractions, or other muscle activities induced by the electrode array 110. The muscle twitch profile can then be used as feedback in order to facilitate automatic or semi-automatic modulation of the TENS treatment output by the electronics subsystem 140. The muscle twitch sensor subsystem is thus preferably configured to measure a set of muscle twitches induced by the electrode array at the patient, thereby yielding a measured muscle twitch signal characterized by a set of measured muscle twitch values. Preferably, the muscle twitch sensor subsystem 130 enables measurement of the set of muscle twitches non-invasively; however, the muscle twitch sensor subsystem 130 can alternatively enable measurement of the set of muscle twitches invasively or semi-invasively (e.g., with some penetration of the patient's skin, subcutaneously). The muscle twitch sensor subsystem 130 can be configured to detect muscle vibrations mechanically, electrically, optically, and/or by using any other suitable mechanism. Furthermore, the muscle twitch sensor subsystem 130 preferably enables detection of a magnitude and a pattern of the muscle twitch profile, but can alternatively enable detection of any suitable parameter of the muscle twitch profile.

As shown in FIG. 1A, the muscle twitch sensor subsystem 130 preferably comprises an accelerometer 132, which functions to mechanically enable detection of muscle vibrations characterizing the set of muscle twitches. The accelerometer preferably detects vibrations in at least one axis; however, the accelerometer can additionally detect vibrations in multiple axes. As such, the accelerometer 132 is preferably a dual-axis accelerometer (e.g., an X-Y accelerometer); however, the accelerometer 132 can alternatively be a triple axis accelerometer (e.g., an X-Y-Z accelerometer), a single axis accelerometer, or a combination of multiple accelerometers. Preferably, the accelerometer 132 is located proximal to one of the first and the second electrodes 112, 114; however, the accelerometer can alternatively be located at or integrated with any other suitable element of the system 100, such as the electronics subsystem. In one variation, the accelerometer 132 is integrated with one of the first and the second electrodes 112, 114 (e.g., embedded within the electrode), and in another variation, the accelerometer 132 is not integrated with one of the first and the second electrodes 112, 114 in order to facilitate modular and disposable aspects of the system 100. The muscle twitch sensor subsystem 130 preferably also comprises a second accelerometer 132', as shown in FIG. 1A, which functions to build sensor redundancy into the system in order to build robustness into the system 100 and to provide a safety mechanism for the system 100. In one example of redundancy, if the one of the accelerometers 132 fails, the other accelerometer 132' can still detect vibrations in order to provide feedback to the electronics subsystem 140.

The muscle twitch sensor subsystem 130 can additionally or alternatively comprise an electromyography (EMG) sensor 134, which functions to electrically enable detection of muscle vibrations characterizing the set of muscle twitches. The EMG sensor 134 measures electrical potentials generated by muscle cells when the muscle cells are activated, and operates using electrodes that are brought into close contact with the muscle(s) of interest. Preferably, the EMG sensor 134 is a non-invasive surface EMG (sEMG) sensor that is configured to interface with the patient's skin; however, in other variations, the EMG sensor 134 can be an implanted EMG sensor that is positioned subcutaneously or is implanted directly into a muscle or muscle group of interest. Preferably, the EMG sensor 134 is implemented using the electrode array no and the control module 155, wherein the control module 155 is configured to read voltage differences between electrodes of the electrode array 110 while a current is being injected through electrodes of the electrode array no. Alternatively, the EMG sensor 134 can be a standalone unit and can be placed proximal to one of the first and the second electrodes 112, 114, integrated with one of the first and the second electrodes 112, 114, or can be configured in any other suitable manner relative to the first and the second electrodes 112, 114, as shown in FIG. 1A. Similar to the redundancy provided by multiple accelerometers 132, the muscle twitch sensor subsystem 130 can also comprise multiple EMG sensors 134 system in order to build robustness into the system 100 and to provide a safety mechanism for the system 100.

The muscle twitch sensor subsystem 130 can additionally or alternatively comprise an audio sensor, which functions to enable mechanical (acoustic) detection of muscle vibrations characteristic of the set of muscle twitches. The audio sensor can be a microphone, which enables detection of sound waves generated by a twitching muscle, but can be any other suitable sensor that enables acoustic detection of muscle vibrations. Preferably, the audio sensor is positioned proximal to one of the first and the second electrodes 112, 114; however, the audio sensor can alternatively be positioned at any suitable location or integrated with any suitable element of the system 100 (e.g., the electronics subsystem) such that sufficient acoustic detection of muscle vibrations is enabled. Again, the muscle twitch sensor subsystem 130 can also comprise multiple audio sensors to build redundancy and robustness into the system 100.

The muscle twitch sensor subsystem 130 can comprise any suitable combination of the sensor variations (i.e., type, number, position, configuration), and/or can comprise additional sensors or sensor types (e.g., optical sensors) to enable detection of vibrations characteristic of the set of muscle twitches. Again, sensors of the muscle twitch sensor subsystem 130 are preferably configured to facilitate modular and/or disposable aspects of the system 100, but can alternatively be integrated within disposable elements of the system 100 (e.g., electrodes) in the interest of providing better signal quality from the sensor(s). In one variation, the sensor(s) of the muscle twitch sensor subsystem 130 are coupled to the electronics subsystem 140 through the connector 120, and in specific examples, electrical wiring for the sensor(s) of the muscle twitch sensor subsystem 130 passes through a retractable cable 121 and/or a flexible sliding track 123.

1.4 Electronics Subsystem

As shown in FIGS. 1A and 1B, the electronics subsystem 140 comprises a power module 145 configured to power the system 100, a pulse generator 150 coupled to the electrode array no and configured to transmit the TENS treatment, and a control module 155 configured to facilitate modulation of the TENS treatment, thereby managing patient pain. The electronics subsystem 140 functions to modulate a parameter of the TENS treatment based upon the set of measured muscle twitch values from the muscle twitch sensor subsystem 130, until a threshold is satisfied, thereby managing pain of the patient. The electronics subsystem 140 can thus receive an input from the muscle twitch sensor subsystem 130, characterizing the set of muscle twitches, and can modulate a parameter of the TENS treatment based upon the input until an adjusted muscle twitch profile detected at the muscle twitch sensor subsystem 130 satisfies the threshold. The electronics subsystem 140 can further function to implement safety mechanisms for the system 100, and in variations, can prevent the system 100 from overheating, from malfunctioning due to open-circuited or short circuited electrodes, and/or from malfunctioning due to faulty components of the muscle twitch sensor subsystem 130. The electronics subsystem 140 can be positioned medially between the first and the second electrodes 112, 114, as shown in FIG. 1B, such that the system 100 has an axis of symmetry, or can be positioned relative to other elements of the system 100 in any other suitable manner.

Preferably, the electronics subsystem 140 complies with relevant technical and safety standards, and in a specific example, complies with International Electrotechnical Commission (IEC) standards 60601-1:2005+A1:2012(E), IEC 60601-1-2 Ed. 3.0, IEC 60601-2-10:2012, and American National Standard Institute (ANSI)/Association for the Advancement of Medical Instrumentation (AAMI) ESI-1985, AAMI NS4:1986® 2009. In other variations, the electronics subsystem 140 can comply with any additional or alternative technical and/or safety standards.

The power module 145 of the electronics subsystem 140 functions to provide regulated and unregulated electrical power to the system 100 and to allow power storage for the system 100. The power module 145 preferably comprises a lithium-ion battery that is configured to be rechargeable, but can alternatively comprise any other suitable rechargeable battery (e.g., nickel-cadmium, metal halide, nickel metal hydride, or lithium-ion polymer). Alternatively, the power module 145 can comprise a non-rechargeable battery (e.g., alkaline battery) that can be replaced to further enhance modularity in the system 100. Preferably, the power module 145 is configured to have a profile with a low aspect ratio, contributing to a thin form factor of the system 100. However, the power module 145 can be configured to have any appropriate profile such that the power module 145 provides adequate power characteristics (e.g., cycle life, charging time, discharge time, etc.) for the system 100.

In variations where the battery of the power module 145 is rechargeable, the electronics subsystem 140 can also comprise a coil of wire and associated electronics that function to allow inductive coupling of power between an external power source and the power module. The charging coil preferably converts energy from an alternating electromagnetic field (e.g., provided by a charging dock or other adapter), into electrical energy to charge the battery and/or to power the system 100. Inductive charging allows electrical isolation between the external power supply and internal electronics to facilitate increased patient safety. Inductive charging provided by the charging coil thus also facilitates patient mobility while interacting with the system 100, such that the patient can be extremely mobile while managing his or her pain with the system 100. In alternative variations, however, the charging coil can be altogether omitted (e.g., in variations without a rechargeable battery), or replaced or supplemented by a connection (e.g., USB connection) configured to provide wired charging of a rechargeable battery.

Figure 6A:
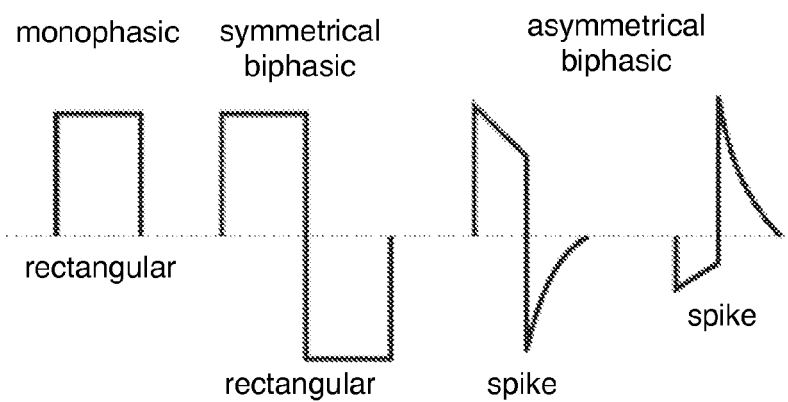
FIGS. 6A-6C depict variations of TENS stimulation parameters of embodiments of a system and method for managing pain of a patient.
Figure 6B:
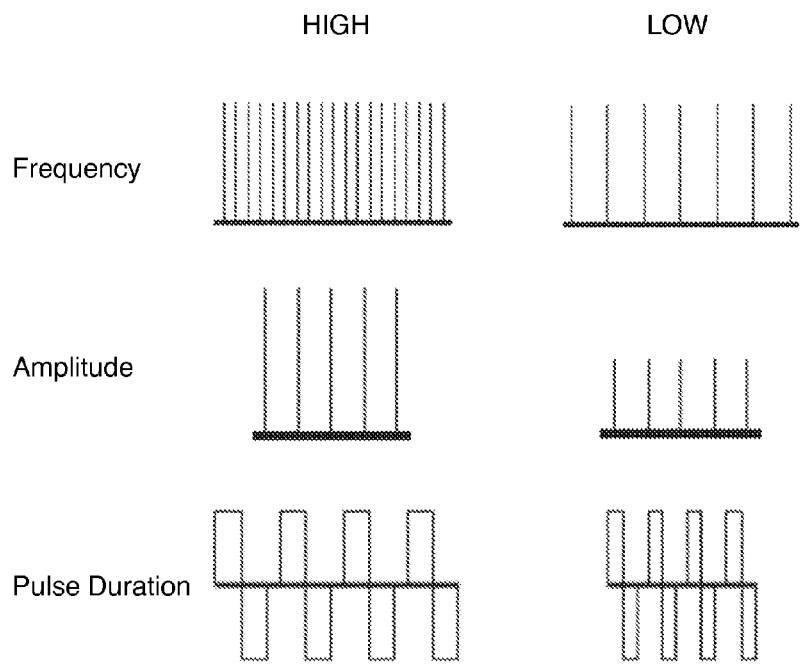
Figure 6C:
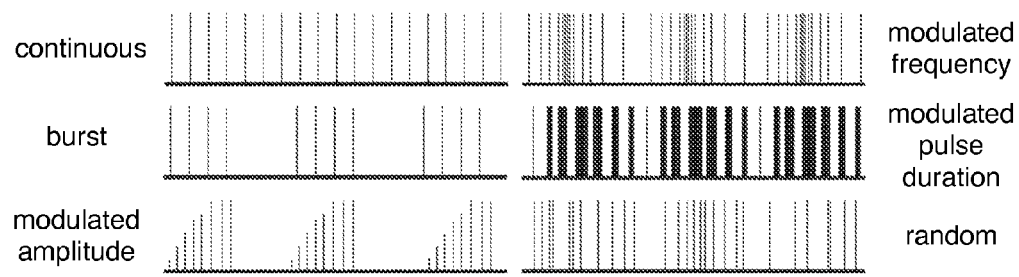

The pulse generator 150 of the electronics subsystem 140 is preferably electrically coupled to the power module 145 and the control module 155, and functions to generate the TENS treatment and provide versatility in the parameters of the TENS treatment. Preferably, the pulse generator 150 can provide a monophasic waveform, a symmetrical biphasic waveform, and an asymmetrical biphasic waveform; however, the pulse generator 150 can alternatively be configured to provide any subset of the described waveforms or any other suitable stimulation profile, as shown in FIG. 6A. The pulse parameters transmitted by the pulse generator 150 preferably comprise pulse amplitude, pulse duration, pulse frequency, pulse shape, and pulse pattern, as shown in FIGS. 6A-6C, but can additionally or alternatively comprise any other suitable parameter(s). In a specific example, the pulse generator is configured to transmit TENS treatments characterized by adjustable pulse amplitudes from 1-50 mA into a 1 kilo-ohm load, pulse durations from 10-1000 microseconds, adjustable pulse frequencies from 1-250 Hz, and pulse patterns that are continuous, burst, of modulated amplitude, of modulated frequency, and/or of modulated pulse duration. In this specific example, the modulated amplitudes, modulated frequencies, and/or modulated pulse durations can be characterized by exponential decay, exponential growth, or any other suitable growth or decay profiles. In another specific example, the pulse generator is configured to transmit TENS treatments characterized by pulse durations from 30-260 microseconds, adjustable pulse frequencies from 20-150 Hz, rectangular biphasic waveforms with a zero net DC component, and pulse patterns characterized by positive phases with constant-current.

The pulse generator 150 preferably delivers TENS treatments (as controlled by the control module 155) that activate large diameter fibers (e.g., using high frequency, low intensity, low amplitude stimulation with a continuous pulse pattern), activate small diameter fibers (e.g., using low frequency, high intensity, high amplitude stimulation with a burst pulse pattern), and/or activate nerves (e.g., afferent nerve fibers) using stimulation with greater intensity (e.g., using high frequency, high intensity, high amplitude stimulation with a continuous pulse pattern). In examples, high frequency stimulation is greater than 80 Hz, low frequency stimulation is ~10-80 Hz, high intensity stimulation has a pulse duration of >1000 microseconds, and low intensity stimulation has a pulse duration of ~100 microseconds. The pulse generator 150 can additionally or alternatively be configured to deliver electrical muscle stimulation (EMS) treatments, which functions to provide an additional pain management function. In examples, the EMS treatments can be configured to treat pain associated with denser muscles/muscle groups, such as lower back pain. The pulse generator 150 can additionally or alternatively be configured to deliver any other suitable electrical treatment.

The control module 155 of the electronics subsystem 140 is preferably coupled to electrodes 112, 114 of the electrode array no, coupled to the muscle twitch sensor subsystem 130, and coupled to the pulse generator 150. The control module 155 functions to receive inputs from the muscle twitch sensor subsystem 130, and to adjust one or more parameters of the TENS treatment, as facilitated by the pulse generator 150 and the electrode array no. The input(s) from the muscle twitch sensor subsystem can be received continuously, intermittently, in real time, in non-real time, or in any other suitable manner. Preferably, the control module 155 adjusts or modulates the parameter(s) of the TENS treatment, based upon the input(s), until an adjusted muscle twitch profile detected at the muscle twitch sensor subsystem 130 satisfies a threshold value. Thus, the control module 155 is preferably in continuous communication with the muscle twitch sensor subsystem 130 while the system 100 is active, such that continuous feedback is available to the control module 155 to modulate the TENS treatment parameter(s). The control module 155 preferably automatically modulates the TENS treatment, but in some variations, can be overridden manually, such that the patient or other entity can provide manual control of the TENS treatment. The control module 155 thus preferably comprises a microprocessor and a voltage regulator, and can additionally comprise or be coupled to any other suitable element(s), such as an analog-to-digital converter (e.g., to convert analog signals from the muscle twitch sensor subsystem), an amplifier, and/or a filter for processing signals prior to reception by the control module 155.

The control module 155 preferably maintains a level of stimulation, as indicated by the muscle twitch profile or measured muscle twitch values derived from a measured muscle twitch signal, wherein the threshold level of stimulation is therapeutic for pain management purposes. Alternatively, the control module 155 can be configured to bring the patient to any suitable level of stimulation. The level of stimulation is preferably patient-specific and can be induced within the range of parameters provided by the pulse generator 150. The level of stimulation can be determined empirically upon initializing the system 100 by the patient, and in one variation, the control module 155 can provide a range of parameters for each treatment parameter in order to provide the patient with a pain management treatment personalized to the patient. In this variation, the control module 155 can be configured to overshoot a parameter value, such that the patient experiences a safe level of discomfort from the stimulation, and then to decrease the parameter until the patient reaches an appropriate level of stimulation for pain management. Conversely, the control module 155 can alternatively be configured to ramp or step up a parameter level until the stimulation reaches an appropriate level for pain management. The personalized treatment can be associated with different activities of the patient, different body regions of the patient, different configurations of the electrode array 110, and/or different times (e.g., treatments can be associated with different times of the day, different weeks, etc.) and can additionally be saved, in a manner that contributes to a comprehensive pain management regimen for the patient. The threshold level of stimulation can additionally or alternatively be predetermined (e.g., during a medical consultation or by clinical studies of patients with similar injuries), or can be determined using any other suitable method. Furthermore, the threshold level of stimulation can be adjusted over time in order to prevent and/or counteract declining patient response to the TENS treatment. In an example, the TENS treatment parameters (e.g., frequency, total duration, pulse duration, amplitude, intensity) can be drastically or gradually varied daily or weekly, such that the patient never fully acclimates to a given TENS treatment, and so that the TENS treatment remains effective for the patient over time.

The level of stimulation can be associated with any suitable parameter or combination of parameters, as detected using the muscle twitch sensor subsystem 130. Preferably, the level of stimulation is associated with an amplitude of the muscle twitch profile waveform (e.g., the level of stimulation is determined by a threshold amplitude value of the measured muscle twitch signal or a derivative thereof), such that the control module 155 modulates the TENS treatment parameter(s) to maintain the amplitude of the muscle twitch profile as the patient moves or otherwise performs activities. In variations, wherein the amplitude of the muscle twitch profile or a measured muscle twitch signal, is non-uniform over given cycles of stimulation, an average amplitude value of the muscle twitch signal (or derivative thereof) can be compared to a threshold and the control module 155 can modulate the TENS treatment accordingly. In other variations, the threshold can be associated with a combination of the amplitude, the frequency, and/or any other suitable parameter of muscle stimulation (e.g., by a mathematical algorithm that uses the amplitude, the frequency, and/or any other suitable parameter(s) as variables), such that the threshold is a threshold value of stimulation based upon a combination of parameters. The threshold can, however, be a threshold value of any other single parameter that can be detected from the muscle twitch profile using any sensor of the muscle twitch sensor subsystem 130.

Furthermore, the threshold can be a threshold value or a threshold range of values, such that the control module 155 is configured to maintain a muscle twitch profile parameter (e.g., frequency, amplitude, combination of parameters, average value of parameter(s)) at a threshold value or within a threshold range of values, wherein the threshold range of values is defined by a first limiting value and a second limiting value. Maintaining a muscle twitch profile parameter within a threshold range can be performed in a manner that is inclusive of a limiting value, such that a muscle twitch profile parameter satisfies the threshold range even if the muscle twitch profile parameter is substantially equivalent to the limiting value. Alternatively, maintaining a muscle twitch profile parameter within a threshold range can be performed in a manner that is exclusive of a limiting value, such that a muscle twitch profile parameter does not satisfy the threshold range if the muscle twitch profile parameter is substantially equivalent to the limiting value. In one variation, the control module 155 can be configured to modulate a parameter of the TENS treatment until a muscle twitch profile parameter satisfies a threshold value. In another variation, the control module 155 can be configured to modulate a parameter of the TENS treatment when a muscle twitch profile parameter reaches a first limiting value of a threshold range, such that the muscle twitch profile parameter does not reach or exceed a second limiting value of the threshold range. In this variation, the control module 155 can be configured to additionally or alternatively modulate a parameter of the TENS treatment when the muscle twitch profile parameter reaches or exceeds the second limiting value of the threshold range. The control module 155 can, however, be configured to modulate the TENS treatment in any other suitable manner.

Figure 10A:
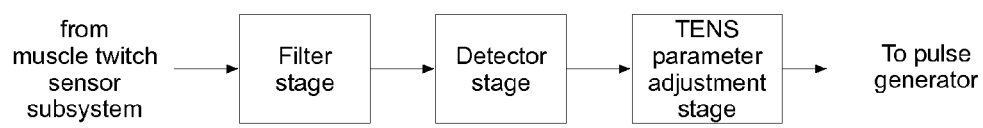
FIGS. 10A and 10B depict variations of a method for filtering muscle twitch signals in order to manage pain of a patient.
Figure 10B:
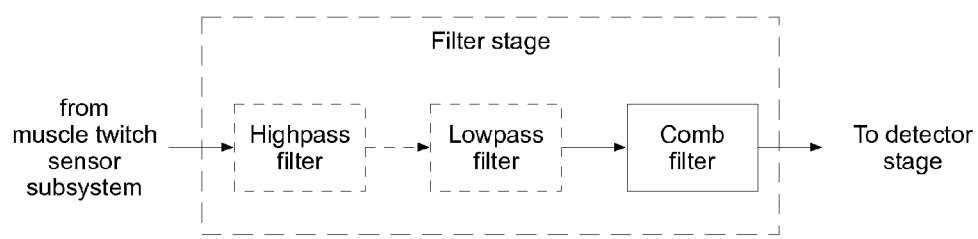

In one variation, as shown in FIGS. 10A and 10B, the control module 155 can be configured to pass signals from the muscle twitch sensor subsystem 130 through a filter stage and can additionally or alternatively be configured to pass signals through a detector stage, such that a subsequent TENS parameter adjustment stage can appropriately adjust a parameter (e.g., an intensity) of the TENS treatment generated by the pulse generator 150. The adjustment of TENS treatment parameters based upon a comparison to a threshold can therefore be based upon a derivative of the measured muscle twitch values, and/or a processed measured muscle twitch signal. The pulse generator 150 provides electrical stimulation at a specific frequency. If the stimulation amplitude is high enough, the patient's motor nerve fibers will be stimulated in addition to the A-beta sensory fibers; this can be indicative of a "strong but comfortable" stimulation amplitude. During calibration, a relatively low stimulus frequency (e.g., below approximately 20 Hz) induces vibration of the skin at the stimulus frequency; generally, the skin will also vibrate at harmonics of the stimulus frequency. The filter stage is thus configured to amplify the signals from the muscle twitch sensor subsystem 130 at the stimulus frequency and, additionally or alternatively, its harmonics, in order to distinguish TENS-induced muscle vibration from other forms of muscle activity and noise.

In one variation of the filter stage, a bandpass filter can be used to amplify the signals of the muscle twitch sensor subsystem (e.g., accelerometer signals) at the stimulus frequency and/or attenuate signals at other frequencies. In another variation of the filter stage, as shown in FIG. 10B, a DC-blocking highpass filter (e.g., a fifth-order infinite impulse response (IIR) filter) can be used to remove very low-frequency noise. The output of the highpass filter is optionally sent to a lowpass filter (e.g., a second-order IIR filter having a lowpass cutoff at approximately three times the stimulus frequency) in order to remove high-frequency noise. In this variation, the resulting signal can then be sent to an IIR peak comb filter having narrow peaks at DC (e.g., 0 Hz), the stimulus frequency, and each of the stimulus frequency's harmonics. In one variation, the comb filter has the difference equation: $y(t)=kx(t)+(1-k)y(t-D)$, where $x(t)$ is the optionally highpassed and/or lowpassed muscle twitch sensor subsystem 130 signal (e.g., accelerometer signal) as a function of time t, $y(t)$ is the comb filtered output signal, D is a delay that equals the sample rate divided by the stimulus rate and rounded to the nearest integer, and k is a constant (e.g., k=0.10) chosen for a good compromise between the width of the peaks, the depth of the attenuation, the smoothness of the response, and the latency of the response. Since the DC-blocking highpass signal will remove the energy around 0 Hz, the energy of the output of the comb filter is indicative of the amount of TENS-induced muscle vibration at the stimulus frequency and its harmonics. Other filters, such as filters based on the fast Fourier transform (FFT), short-time Fourier transform (STFT), Goertzel algorithm, or sliding discrete Fourier transform (SDFT), and/or another other suitable filter can be used at the filter stage.

In another variation of the filter stage, in order to better distinguish between the TENS-induced muscle vibration and other forms of muscle activity and noise, the filter stage can additionally include a notch filter (for example, a notch comb filter) in parallel with the peak comb filter. The notch filter is preferably complementary to the peak comb filter and is characterized by a difference equation such as: $n(t)=(1-k)x(t)-(1-k)x(t-D)+(1-k)n(t-D)$, where $n(t)$ is the notch comb filtered output signal, and the other parameters are as described above. The energy of the output of the notch comb filter is representative of non-TENS-induced muscle activity and noise at frequencies other than the stimulus frequency and its harmonics. By comparing the outputs of the peak comb filter and the notch comb filter, the detector stage can distinguish TENS-induced muscle vibration from other forms of muscle activity and noise.

As described earlier, an output of the filter stage can be sent to a detector stage, which functions to detect an amount of TENS-induced muscle vibration. In one variation, the detector stage comprises of an envelope follower. In one example of this variation, the envelope follower performs a running root-mean-square (RMS) operation by squaring the output of the filter stage, implementing a first-order IIR smoothing filter on the squared values, and taking the square root of the result. In another variation, a first-order smoothing filter instead operates on the absolute value of the output of the filter stage, in order to avoid the squaring operation that can result in signals having too large a dynamic range to be handled easily by a low-bit-depth processor or microcontroller; in this variation, no square root operation would be needed, resulting in significantly reduced processor requirements.

The TENS parameter adjustment stage, as governed by the control module 155, is preferably configured to adjust the TENS stimulus intensity (for example, the amplitude of the current) of the pulse generator 150 based upon an output of the detector stage. In one variation, the pulse generator 150 can be configured to increment the stimulus amplitude whenever an output of the detector stage is below a given target (e.g., threshold) value, and decrement the stimulus amplitude whenever an output of the detector stage is above the target (e.g., threshold) value. In another variation, hysteresis can be used to avoid excessive adjustment of the stimulus amplitude. In another variation, stimulus amplitude can be incremented or decremented in proportion to a distance between the instantaneous value of the output of the detector stage and the target (e.g., threshold) value, such that only small adjustments are made when the output of the detector stage is close to the target (e.g., threshold) value.

The control module 155 can also function to provide an additional safety mechanism for the system. In one variation, the control module 155 can provide periodic output of test pulses (as enabled by the pulse generator 150), in order to detect muscle twitch responses induced by the test pulses (as enabled by the muscle twitch sensor subsystem 130). If the muscle twitch sensor subsystem 130 does not indicate a response to the test pulses, the control module 155 can be configured to terminate the TENS treatment (or adjust of the TENS treatment), due to faulty feedback provided by a failed muscle twitch sensor subsystem 130. In another variation, unusual inputs provided by the muscle twitch sensor subsystem 130 can be used to modulate or terminate the TENS treatment, as another safety mechanism. In a specific example of this variation, gross movements, as detected by accelerometers 132 of the muscle twitch sensor subsystem 130 can indicate that the patient is having an unexpected response to the TENS treatment and result in termination of the TENS treatment. In another variation, the control module 155 can limit the total duration of the TENS treatment, and in a specific example, limits the total treatment time to 30 minute durations followed by rest periods, in order to effectively manage the patient's pain treatment regimen. In an alternative to this variation, the control module 155 can be configured to automatically terminate the TENS treatment if a parameter of the TENS treatment (e.g., frequency, pulse duration, amplitude, intensity) is at a maximum level for a certain period of time (e.g., 10 minutes), if the power module 145 is in a charging state, and/or if the electrodes become detached from the patient.

The control module 155 can also receive an input from a deformation sensor and/or a position sensor (e.g., of the connector 120, coupled to the connector 120, coupled to the electrode array 110), wherein the input characterizes placement of the electrode array 110 on the patient. The deformation sensor and/or position sensor can, for example, enable determination that the electrode array 110 is placed on a curved region of the patient's body, and, in combination with an input from the muscle twitch sensor subsystem 130, can be used to enable modulation of the TENS treatment in response to the position and/or configuration of the electrode array no. In other variations, data from the deformation and/or position sensor can be used to guide placement of the electrode array no, in order to improve the stability, effectiveness, or robustness of the TENS treatment provided by the electronics system 140.

The electronics subsystem 140 can additionally or alternatively comprise any other suitable element that facilitates modulation of the TENS treatment or provides an additional safety mechanism for the system 100. Furthermore the electronics subsystem 140 can be coupled to a user control module 158 that interfaces with the electronics subsystem 140, such that manual control of the TENS treatment can be performed by the patient or any other suitable entity. The user control module 158 can comprise a power toggle (e.g., on/off button) for initiating the TENS treatment, for calibration of the system 100, and/or for termination of the TENS treatment. The user control module 158 can further comprise controllers (e.g., dials, panels, sliders, knobs) for modulation of other stimulation parameters (e.g., frequency, amplitude, intensity, pulse duration, pulse pattern, total duration). Preferably, the user control module 158 provides a minimal number of controls (e.g., an on/off button, a stimulation increasing button, and a stimulation decreasing button), but can provide any suitable number of manual controls. The user control module 158 can be touch-activated (e.g., with a touch screen, buttons, dials, knobs, sliders), or can be activated using any other suitable manner (e.g., sound activation). Preferably, the control module is integrated with the electronics subsystem 140, and in one embodiment, is located medially between electrodes 112, 114 of the electrode array 110, proximal to the electronics subsystem 140, as shown in FIGS. 1B and 2. Additionally, the patient or other entity is preferably able to operate the user control module 158 even with limited visualization of the user control module 158; however, the user control module 158 can, in alternative variations, require visualization for operation. In still other alternative variations, the user control module 158 can be implemented remotely from the system 100, for example, using an application executing on a mobile device 161 of the patient.

1.5 System—Other Elements

As shown in FIG. 1A, the system 100 can further comprise a data link 160, coupled to the electronics subsystem 140, which functions to transmit an output of at least one element of the electronics subsystem 140 to a mobile device 161 or other computing device (e.g., desktop computer, laptop computer, tablet, smartphone, health tracking device). Preferably, the data link 160 is a wireless interface; however, the data link 160 may alternatively be a wired connection. In a first variation, the data link 160 can include a Bluetooth module that interfaces with a second Bluetooth module included in the mobile device 161 or external element, wherein data or signals are transmitted by the data link 160 to/from the mobile device 161 or external element over Bluetooth communications. The data link 160 of the first variation can alternatively implement other types of wireless communications, such as 3G, 4G, radio, or Wi-Fi communication. In the first variation, data and/or signals are preferably encrypted before being transmitted by the data link 160. For example, cryptographic protocols such as Diffie-Hellman key exchange, Wireless Transport Layer Security (WTLS), or any other suitable type of protocol may be used. The data encryption may also comply with standards such as the Data Encryption Standard (DES), Triple Data Encryption Standard (3-DES), or Advanced Encryption Standard (AES).

In a second variation, the data link 160 is a wired connection, wherein the data link includes a wired jack connector (e.g., a ⅛" headphone jack) such that the electronics subsystem 140 can communicate with the mobile device 161 and/or any external computing element through an audio jack of the mobile device 161 and/or external computing element. In one specific example of the data link 160 that includes a wired jack, the data link 160 is configured only to transmit output signals from the electronics subsystem 140. In another specific example, the data link 160 is configured to transmit data to and from at least one element of the electronics subsystem 140 and a mobile device 161. In this example, the data link 160 can transmit output signals into the mobile device 161 through the microphone input of the audio jack of the mobile device 161 and can retrieve data from the audio output of the audio jack of the mobile device 161. In this example, the data link 160 may communicate with the mobile device 161 via inter-integrated circuit communication ($I_2C$), one-wire, master-slave, or any other suitable communication protocol. However, the data link 160 can transmit data in any other way and can include any other type of wired connection (such as a USB wired connection) that supports data transfer between the electronics subsystem 140, the mobile device 161, and/or any other suitable computing element.

Also shown in FIGS. 1A and 2, the system 100 can further comprise a housing 170 configured to enclose at least a portion of the system 100. The housing functions to protect elements of the system 100 over the lifetime usage of the system 100, and can further function to enhance wearability of the system 100. In some variations, the housing 170 can further function to provide instructions to a patient (e.g., with a text label and/or a schematic label) at a surface of the housing 170. Preferably, the housing 170 is flexible to facilitate adhesion to the patient as the patient moves; however, the housing 170 can alternatively be rigid. In an embodiment where the housing 170 is flexible, other elements of the system 100 can also be flexible (e.g., the power module 145 can comprise a flexible thin film battery, the electronics subsystem 140 can comprise flexible electronics, etc.) to facilitate adhesion to the patient. The housing 170 can further comprise an adhesive layer or other element that facilitates adherence of the system 100 to the patient. The housing 170 can additionally comprise multiple housings, and in one variation, comprises a housing for the electronics subsystem 140 and the user control module 158, and a housing for each of the electrodes of the electrode array no. In this variation, the housings for the electrodes of the electrode array no can be configured to mechanically couple to the electrodes (e.g., the first and the second electrodes 112, 114), wherein the mechanical coupling also stabilizes an electrical connection between an electrode and the electronics subsystem 140. In this variation, the electrodes can also be reversibly coupled to the housing(s), in order to facilitate modular and/or disposable features of the system 100. In alternative variations, the system 100 can comprise a single housing for the electronics subsystem 140 and/or the user control module 158, without housings for the electrodes of the electrode array 110.

Figure 7A:
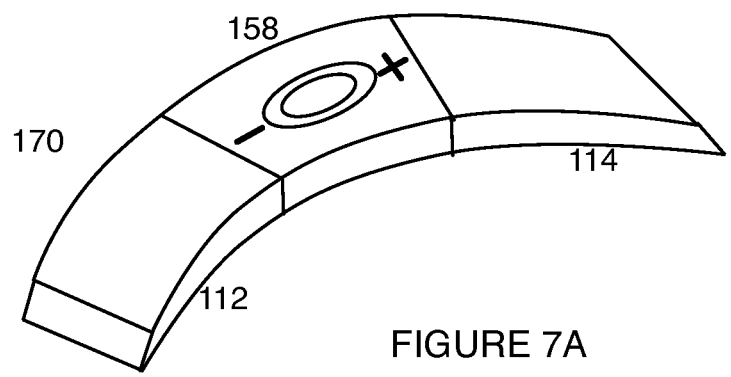
FIGS. 7A and 7B depict examples of systems for managing pain of a patient.
Figure 7B:
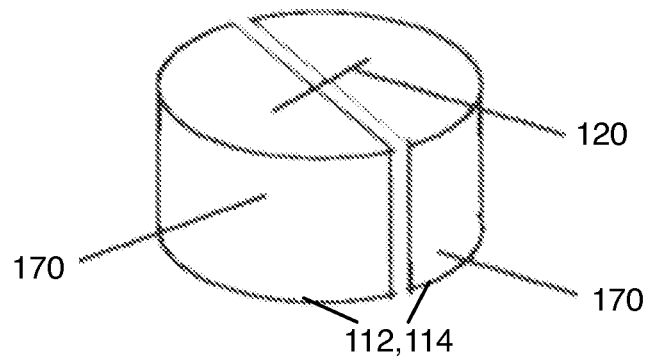

In one example, the housing 170 is characterized by a bandage-like, flexible, thin form factor that is configured to facilitate wearability by the patient and adhesion to the patient. As shown in FIG. 2, the housing 170 protects the electronics subsystem 140 and the user control module 158, and is positioned medially between a first housing that houses first electrode 112 and a second housing that houses second electrode 114. In the example, the connector 120 is a retractable cable 121 with a pinwheel 122, and the connector 120 is coupled, through the housing, to each of the first housing and the second housing. The retractable cable 121, along with the pinwheel 122, thus allows a distance between the electronics subsystem 140 and the electrodes 112, 114 to be extended. The retractable cable 121 further allows the electrodes to be displaced from an axis through the electrodes 112, 114 and the electronics subsystem 140, and to rotate away from the axis to facilitate placement of the system 100 at the patient. In the specific example, the housing, the first housing and the second housing do not exceed 0.4 inches in thickness, and each of the housing, the first housing, and the second housing is defined by a square profile (2 inches×2 inches) with rounded corners). The housings of the specific example are composed of a thin, flexible, biocompatible polymer (e.g., polyethylene, nylon) that can additionally be processed to be water resistant or waterproof. In other examples, the housing(s) can comprise any suitable form factor (e.g., rectangular, ellipsoidal, polygonal, triangular), and in examples, as shown in FIGS. 7A and 7B, each electrode housing is characterized by a polygonal profile (FIG. 7A) or a hemi-ellipsoidal profile (FIG. 7B).

The system 100 can additionally further comprise a data storage unit 180, which functions to retain data generated during use of the system 100. The data storage unit 180 may be implemented with the electronics subsystem 140, mobile device 161, personal computer, web browser, external server (e.g., cloud), and/or local server, or any combination of the above, in a network configured to transmit, store, and receive data. Preferably, data from the data storage unit 180 is automatically transmitted to any appropriate external device continuously; however, data from the data storage unit 180 can alternatively be transmitted intermittently (e.g. every minute, hourly, daily, or weekly). In one example, data generated by any element may be stored on a portion of the data storage unit 180 when the data link 160 is not coupled to an element external to the electronics subsystem 140. However, in the example, when a link is established between the data link 160 and an external element, data may then be automatically transmitted from the storage unit 180. In other examples, the data storage unit 180 can alternatively be manually prompted to transmit stored data by a user or other entity.

As a person skilled in the field of pain management devices will recognize from the previous detailed description and from the figures and claims, modifications and changes can be made to the embodiments, variations, examples, and specific applications of the system 100 described above without departing from the scope of the system 100.

2. Method

Figure 8A:
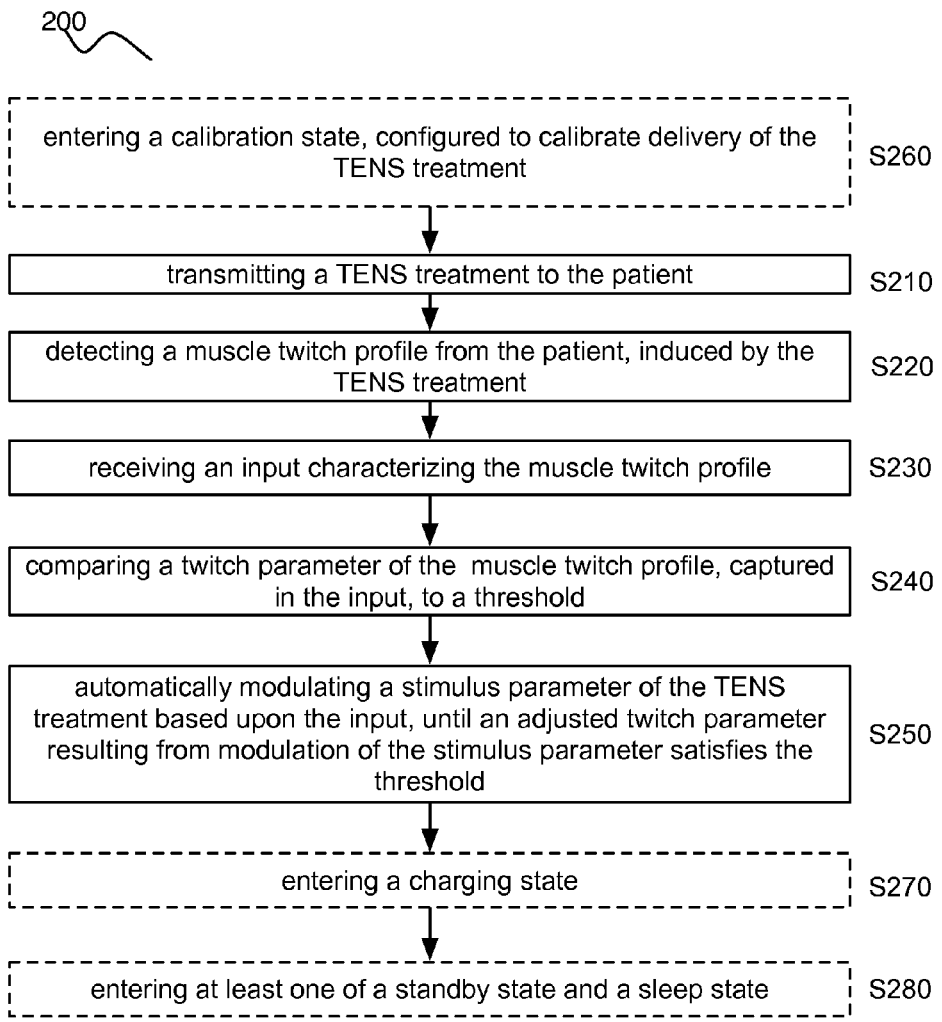
FIGS. 8A and 8B depict embodiments of a method for managing pain of a patient.
Figure 8B:
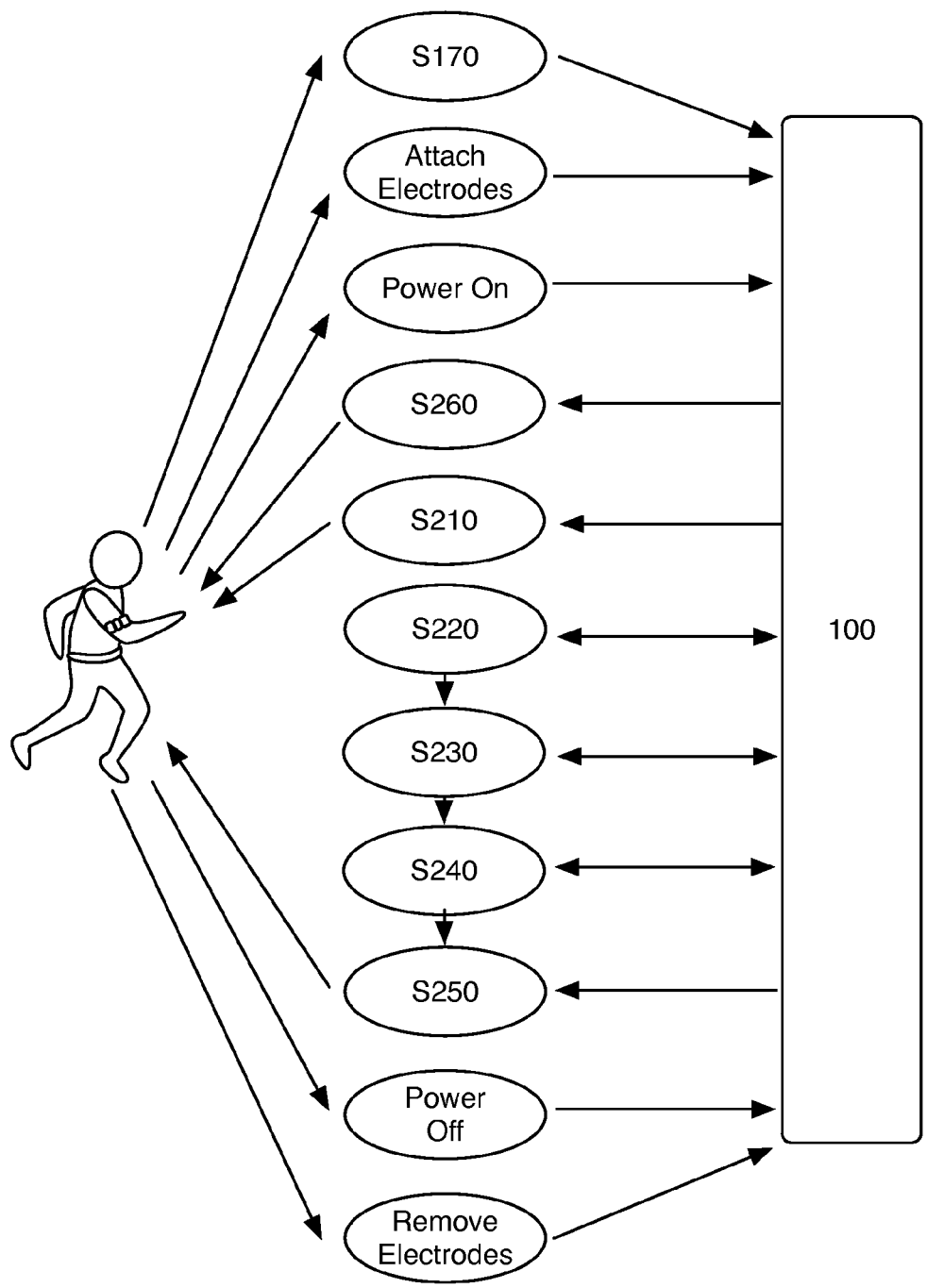

As shown in FIGS. 8A and 8B, an embodiment of a method 200 for managing pain of a patient comprises transmitting a TENS treatment to the patient, wherein the TENS treatment is characterized by a set of treatment parameters S210, detecting a muscle twitch profile from the patient, induced by the TENS treatment S220, at a control module, receiving an input characterizing the muscle twitch profile S230; comparing a twitch parameter of the muscle twitch profile, captured in the input, to a threshold S240; and at the control module, automatically modulating a stimulus parameter of the TENS treatment based upon the input, until an adjusted twitch parameter resulting from modulation of the stimulus parameter satisfies the threshold S250. The method can further comprise entering a calibration state, configured to calibrate transmission of the TENS treatment S260; entering a charging state S270, and entering at least one of a standby state and a sleep state S280.

The method 200 functions to provide a self-regulating, adaptable, and automated pain management process for the patient. Furthermore, the method 200 preferably functions to enable management of a patient's musculoskeletal pain associated with, for example, sore or aching muscles of the lower back, arms or legs due to strain from exercise, work activities, or injury. The method 200 is preferably configured to reduce a patient's pain level, but can alternatively be used to prevent a patient from entering a state of pain, be used to adjust a patient's pain tolerance, and/or be used in any other suitable manner to adjust a patient's experience or sensation of pain. Additionally, the method 200 can function to manage a patient's chronic pain symptoms, and can additionally or alternatively function to manage a patient's acute pain symptoms. Preferably, the method 200 is configured to provide pain management outside of a clinical (e.g., hospital) or research (e.g., laboratory) setting, such that the patient can be in a non-contrived environment as he or she is receiving the TENS treatment.

Preferably, at least a subset of the method 200 is implemented using a portion of the system 100 described above; however, the method 200 can be implemented using any other suitable pain management system configured to provide an adjustable TENS treatment. In one specific example, the method 200 is implement using a unitized system 100 that adheres to the patient (thus not compelling the patient to hold any part of the system 100 by hand), has a low, bandage-like profile that conforms to the patient, and is configured to deliver TENS treatment in an automatically modulated manner to a patient who is substantially removed from clinical/research staff.

Block S210 recites: transmitting a TENS treatment to the patient, wherein the TENS treatment is characterized by a set of treatment parameters. Block S210 functions to provide a modifiable set of treatment parameters that can further be modulated to maintain a threshold level of stimulation for the patient. The set of treatment parameters can comprise a frequency, amplitude, pulse duration, intensity, and total duration, and can additionally or alternatively comprise any other suitable parameter(s). In a specific example, the TENS treatment can be characterized by adjustable pulse amplitudes from 1-50 mA into a 1 kilo-ohm load, pulse durations from 10-1000 microseconds, adjustable pulse frequencies from 1-250 Hz, and pulse patterns that are continuous, burst, of modulated amplitude, of modulated frequency, and/or of modulated pulse duration. Furthermore, the TENS treatment can be monophasic, asymmetrical biphasic, symmetrical biphasic, or of any suitable pattern. The TENS treatment provided in Block S210 is preferably provided using an embodiment of the system 100 above, and specifically at an electrode array coupled to a control module, but can alternatively be provided using any other suitable system configured to provide a TENS treatment. The TENS treatment can be patient specific, activity specific, body region specific, and/or time of day specific, and data characterizing the TENS treatment settings can be stored and/or retrieved to further enhance personalization of the TENS treatment for the patient.

Block S220, which recites: detecting a muscle twitch profile from the patient, induced by the TENS treatment, functions to measure a set of muscle twitches, thereby obtaining a measured muscle twitch signal characteristic of a muscle response to the TENS treatment provided in Block S210. The data characteristic of the muscle response to the TENS treatment can then be used as feedback for modulation of the TENS treatment, such that a threshold level of stimulation is maintained, or such that the method 200 brings the patient to any suitable threshold level of stimulation. The muscle twitch profile is preferably detected using an embodiment of the muscle twitch sensor subsystem described above, but can alternatively be detected using any other suitable sensor system in variations of Step S220. In specific examples, the muscle twitch profile can be detected mechanically using an accelerometer and/or a microphone, detected electrically using an EMG sensor, and/or detected optically using a suitable optical sensor. The muscle twitch profile is preferably characterized by an amplitude and a pattern (e.g., frequency, wavelength, characteristic peaks, etc.), but can alternatively be characterized by any other suitable parameter that characterizes muscle twitching or muscle vibration.

Block S230, which recites: at a control module, receiving an input characterizing the muscle twitch profile, functions to receive the measured muscle twitch signal in order to enable comparison of derivative parameters of the set of muscle twitches induced by the TENS treatment, to a threshold for modulation of the TENS treatment. In Block S230, the input can be directly transmitted from a muscle twitch sensor subsystem to the control module, as shown in FIGS. 1A and 8A, or can alternatively be received from another suitable element, such as a storage module configured to store data associated with the muscle twitch profile(s). The input is preferably continuously received while the TENS treatment is being provided, and is preferably received substantially in real-time, such that real-time feedback from a muscle response to the TENS treatment can be used to modulate the TENS treatment. However, in alternative variations, the input can be intermittently received or received in a non-continuous manner, and can further be received in non-real time.

Block S240, which recites: comparing a twitch parameter of the muscle twitch profile, captured in the input, to a threshold, functions to generate a comparison that can be used as the basis for modulating the TENS treatment. The threshold in Block S240 can be a threshold level of stimulation associated with any suitable parameter or combination of parameters, as detected using an embodiment of the muscle twitch sensor subsystem described above. Preferably, the threshold level of stimulation is associated with an amplitude of the muscle twitch profile waveform (e.g., the threshold is a threshold amplitude value of the muscle twitch profile), such that the control module 155 modulates the TENS treatment parameter(s) to maintain the amplitude of the muscle twitch profile as the patient moves or otherwise performs activities that adjust the induced stimulation provided by the TENS treatment. In variations, wherein the amplitude of the muscle twitch profile is non-uniform over given cycles of stimulation, an average amplitude value can be compared to the threshold amplitude of muscle stimulation and the control module can modulate the TENS treatment accordingly. The threshold level of stimulation can alternatively be associated with the frequency of the muscle twitch profile (e.g., the threshold is a threshold frequency value of the muscle twitch profile), such that the control module modulates the TENS treatment parameter(s) to maintain the frequency of the muscle twitch profile. Again, an average frequency of the muscle twitch profile can be compared to the threshold frequency in Block S240. In other variations, the threshold can be associated with a combination of the amplitude, the frequency, and/or any other suitable parameter of muscle stimulation (e.g., by a mathematical algorithm that uses the amplitude, the frequency, and/or any other suitable parameter as variables), such that the threshold is a threshold value of stimulation based upon a combination of parameters. The threshold in Block S240 can, however, be a threshold value of any other single parameter that can be detected from the muscle twitch profile using any sensor of the muscle twitch sensor subsystem. Furthermore, the threshold level of stimulation can be adjusted over time in order to prevent and/or counteract declining patient response to the TENS treatment. In an example, the TENS treatment parameters (e.g., frequency, total duration, pulse duration, amplitude, intensity) can be drastically or gradually varied daily or weekly, such that the patient never fully acclimates to a given TENS treatment, and so that the TENS treatment remains effective for the patient over time.

Furthermore, Block S240 can comprise passing a measured muscle twitch signal through at least one of a filter stage and a detection stage, as described in relation to the control module 155 of an embodiment of the system 100 described above, and can comprise any other suitable signal processing stage.

Block S250 recites: at the control module, automatically modulating a stimulus parameter of the TENS treatment based upon the input, until an adjusted twitch parameter resulting from modulation of the stimulus parameter satisfies the threshold. Block S250 functions to maintain a threshold level of stimulation induced by the TENS treatment, and can additionally or alternatively function to bring the patient to any suitable level of stimulation as induced by an adjusted TENS treatment. In variations, a stimulation parameter e.g., frequency, amplitude, pulse duration, pulse pattern, total duration) or combination of stimulation parameters of the TENS treatment can be adjusted in response to the comparison between the muscle twitch profile and the threshold. The stimulation parameter or combination of stimulation parameters can be increased if a twitch parameter of the muscle twitch profile is below the threshold, or the stimulation parameter or combination of stimulation parameters can be decreased if a twitch parameter of the muscle twitch profile is above the threshold. Alternatively, the stimulation parameter or combination of stimulation parameters can be decreased if a twitch parameter of the muscle twitch profile is below the threshold, or the stimulation parameter or combination of stimulation parameters can be increased if a twitch parameter of the muscle twitch profile is above the threshold. Furthermore, multiple stimulation parameters can be simultaneously modulated, or stimulation parameters can be individually or sequentially modulated in Block S250. In one specific example, a determination that an average amplitude of the muscle twitch profile is below a threshold amplitude can be used to increase an intensity and/or a frequency of the TENS treatment.

In Block S250, modulation of the parameter(s) of the TENS treatment to provide an adjusted TENS treatment can alternatively or additionally be based upon position and/or deformation of the electrode array. In one variation, using an embodiment of the system 100 described above, a deformation sensor and/or a position sensor coupled to a connector or any suitable portion of the electrode array can be used to characterize placement of the electrode array on the patient. In one example, the deformation sensor and/or position sensor can enable determination that the electrode array is placed on a curved region of the patient's body, and, alone or in combination with an input from the muscle twitch sensor subsystem, can be used to enable modulation of the TENS treatment in response to the position and/or configuration of the electrode array. In other variations, data from the deformation and/or position sensor can be used to guide placement of the electrode array, such that Step S150 further comprises at least one of guiding placement of the electrode array and adjusting placement of the electrode array based upon a dataset from a position sensor S255. Block S255 can thus improve the stability, effectiveness, or robustness of the TENS treatment provided by the electronics system, by improving placement of the electrode array on the patient.

Figure 9A:
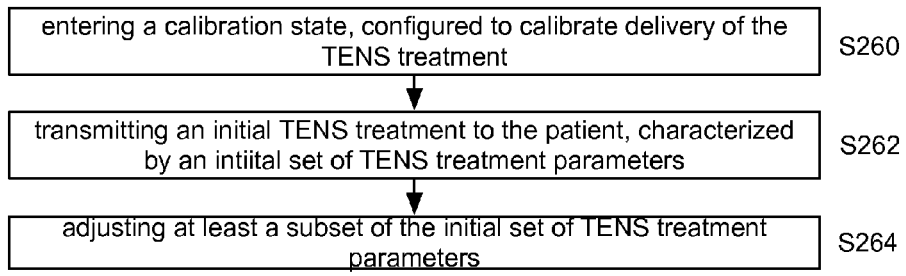
FIGS. 9A and 9B depict variations of a method for managing pain of a patient.

As shown in FIGS. 8A and 9A, the method 200 can further comprise Block S260, which recites entering a calibration state, configured to calibrate transmission of the TENS treatment. Block S260 functions to verify correct function of a system implementing the method 200, and can further function to establish a set of TENS treatment parameters that are patient-specific. As such, Block S260 can comprise transmitting an initial TENS treatment to the patient, characterized by an initial set of TENS treatment parameters (e.g., frequency, amplitude, pulse duration, pulse pattern, total duration) S262, and adjusting at least a subset of the initial set of TENS treatment parameters S264 until a satisfactory set of TENS treatment parameters is determined (e.g., a response from the patient satisfies a calibration threshold), wherein the satisfactory set of TENS treatment parameters characterizes the TENS treatment. In one variation, an initial treatment can be transmitted to the patient in Block S260, and a stimulation parameter can be ramped or stepped down until a satisfactory treatment is determined. In another variation, an initial treatment can be transmitted to the patient in Block S260, and a stimulation parameter can be ramped or stepped up until a satisfactory treatment is determined. Alternatively, the TENS treatment can be predetermined, determined empirically using any other suitable method, or determined based upon a previously conducted research study in order to establish the calibration state. In a specific example, the initial TENS treatment can be characterized by a stimulus amplitude that is 5% of the maximum amplitude, and a pulse frequency below 15 Hz, a pulse duration of 180 microseconds, wherein the stimulus amplitude of the initial TENS treatment is gradually adjusted based upon acceleration and/or voltage measurements from a muscle twitch sensor subsystem. In the specific example, a control module can increase the stimulus amplitude when a measured muscle acceleration at the stimulus frequency is less than a threshold target acceleration (e.g., given maximum current and/or voltage levels). Conversely, in the specific example, a control module can decrease the stimulus amplitude when a measured muscle acceleration at the stimulus frequency is greater than a threshold target acceleration.

Figure 9B:
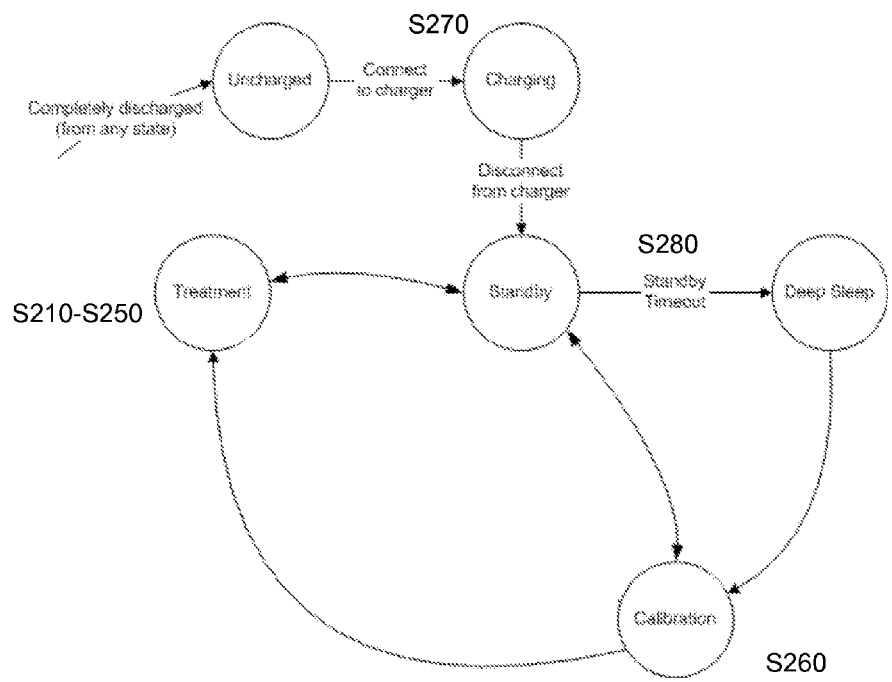

As shown in FIGS. 8A, 8B, and 9B, the method 200 can further comprise Block S270, which recites: entering a charging state. Block S270 functions to charge a system for managing pain of a patient, such that the TENS treatment can be appropriately provided to the patient without interruption. Preferably, the charging state can be entered at any point during implementation of the method 200; however, the charging state can alternatively be entered only when the TENS treatment is being provided, or only when the TENS treatment is not being provided. The charging state can be entered upon placing the system proximal to an inductive charging module, and can additionally or alternatively be entered upon coupling the system to a wired charging module. In Block S270, entering a charging state can pause the TENS treatment, and leaving the charging state can be executed by removing or uncoupling the system from a charging module.

Also shown in FIG. 9B, the method 200 can further comprise Block S280, which recites: entering at least one of a standby state and a sleep state. Block S280 functions to facilitate reduced power consumption in an embodiment of a system implementing a portion of the method 200. The standby state can be entered upon termination of the TENS treatment, wherein termination can be manually performed by an input at a user control module, or automatically performed by a control module (e.g., upon detection of a detached electrode array, or detection of a low-battery condition). The standby state can also be entered upon completion of a provided TENS treatment, upon completion of charging after entering a charging state in Block S260, upon completion of calibration after entering a calibration state in Block S260, and/or upon entering or leaving any other suitable state (e.g., upon completion of data transmission, wirelessly, or using a wired data link). Block S280 can comprise entering a sleep state if the standby state has been experienced for a specified amount of time (e.g., one hour), and/or if a command to enter the sleep state is received.

Variations of the system 100 and method 200 include any combination or permutation of the described components and processes. Furthermore, various processes of the preferred method can be embodied and/or implemented at least in part as a machine configured to receive a computer-readable medium storing computer-readable instructions. The instructions are preferably executed by computer-executable components preferably integrated with a system and one or more portions of the control module 155 and/or a processor. The computer-readable medium can be stored on any suitable computer readable media such as RAMs, ROMs, flash memory, EEPROMs, optical devices (CD or DVD), hard drives, floppy drives, or any suitable device. The computer-executable component is preferably a general or application specific processor, but any suitable dedicated hardware device or hardware/firmware combination device can additionally or alternatively execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

We claim:

1. A system for managing pain, configured to be worn by a patient, comprising:
    a housing that defines a region of an interface between the system and the body of the patient;
    an electrode array comprising a first electrode and a second electrode, coupled to the housing within the region of the interface, for providing a TENS treatment to the patient;
    a muscle twitch sensor subsystem coupled to at least one of the housing and the electrode array and including a vibration sensor configured to measure skin vibrations characterizing a set of muscle twitches induced by the electrode array, from the region of the interface, thereby yielding a measured muscle twitch signal characterized by a set of measured muscle twitch values;
    an electronics subsystem coupled to the housing within the region of the interface comprising a power module configured to power the system, a pulse generator coupled to the electrode array and configured to transmit the TENS treatment to the patient, and a control module configured to receive the measured muscle twitch signal; wherein the electronics subsystem is configured to automatically modulate a parameter of the TENS treatment based upon the set of measured muscle twitch values until a threshold is satisfied, thereby managing pain of the patient; and
    a connector configured to couple at least one of the first electrode and the second electrode to the electronics subsystem.

2. The system of claim 1, wherein at least one of the first electrode and the second electrode comprises a first surface area facing the body of the patient and having a first geometric profile and a second surface area facing the body of the patient and having a second geometric profile different from the first geometric profile, configured to enable detection of resistance changes resulting from differential uncoupling of the first surface area and the second surface area from skin at the interface.

3. The system of claim 1, wherein the electronics subsystem is positioned medially between the first electrode and the second electrode within the housing, and wherein the connector comprises a flexible sliding track configured to enable lateral extension of the first electrode and the second electrode away from the electronics subsystem and lateral contraction of the first electrode and the second electrode toward the electronics subsystem along a linear axis.

4. The system of claim 1, wherein the connector comprises at least one of a deformation sensor and a position sensor configured to generate a dataset characterizing position information of the electrode array, and wherein the electronics subsystem is configured to modulate the parameter of the TENS treatment based upon the dataset.

5. The system of claim 4, wherein the system is configured to guide at least one of the patient and another user in placement of the electrode array based upon the dataset from at least one of the deformation sensor and the position sensor.

6. The system of claim 1, wherein the vibration sensor of the muscle twitch sensor subsystem comprises at least one of a first accelerometer and an audio sensor configured to mechanically measure skin vibrations resulting from the set of muscle twitches, and wherein satisfying the threshold includes providing the TENS treatment at a level that induces skin vibration of the patient that is detectible at the vibration sensor.

7. The system of claim 6, wherein the muscle twitch sensor subsystem further comprises an EMG sensor configured to electrically measure the set of muscle twitches.

8. The system of claim 1, wherein the control module is configured to receive the measured muscle twitch signal from the muscle twitch sensor subsystem substantially continuously and in real time, and wherein the control module is configured to automatically modulate the TENS treatment continuously and in real time, based upon the input.

9. The system of claim 1, wherein the control module is further configured to pass the measured muscle twitch signal through a filter stage, a detector stage, and a TENS parameter adjustment stage.

10. The system of claim 9, wherein the filter stage is configured to distinguish TENS-induced muscle vibration, detected by way of skin vibrations of the patient, from other muscle activity and noise, and comprises a comb filter having peaks at zero Hz, a stimulation frequency of the TENS treatment and each harmonic of the stimulation frequency of the TENS treatment, and a notch filter in parallel with the comb filter.

11. The system of claim 9, wherein the detector stage comprises at least one of an envelope follower configured to perform an infinite impulse response smoothing filter, thereby detecting TENS-induced muscle vibration from skin vibrations of the patient.

12. The system of claim 9, wherein the TENS parameter adjustment stage is configured to increase an amplitude of the TENS treatment when an output of the detector stage is below the threshold, and wherein the TENS parameter adjustment stage is configured to decrease an amplitude of the TENS treatment when an output of the detector stage is above the threshold.

13. The system of claim 1, wherein the electronics subsystem is configured to modulate an intensity of the TENS treatment, based upon a comparison between an amplitude derived from the set of measured muscle twitch values and the threshold.

14. The system of claim 1, further comprising a data link configured to wirelessly transmit at least one of a set of TENS treatment parameters, the set of measured muscle twitch values, a set of parameters derived from the set of measured muscle twitch values, a set of electrical impedance values, a set of electrical resistance values, a set of electrode voltage values, a set of acceleration values, a set of filtered accelerometer values, and a set of battery level values, to a mobile device.

15. The system of claim 14, further comprising a data link configured to wirelessly receive TENS treatment parameters from an application executing at the mobile device, wherein the mobile device is a smart device of patient.

16. A method for managing pain of a patient, comprising:
at an electrode array coupled to a control module, transmitting a TENS treatment, characterized by a first set of stimulus parameters, to the patient at a region of the body of the patient defined by a housing coupled to the electrode array;
at a vibration sensor, measuring skin vibrations characterizing a set of muscle twitches, induced by the TENS treatment, from the patient at a portion of the region of the body defined by the housing, thereby obtaining a measured muscle twitch signal from skin vibrations;
at the control module, receiving the measured muscle twitch signal;
at the control module, detecting a muscle twitch amplitude characterizing the measured muscle twitch signal;
at the control module, generating a comparison based upon the muscle twitch amplitude and a threshold; and
at the control module, automatically modulating a stimulus parameter of the first set of stimulus parameters, based upon the comparison, wherein the stimulus parameter induces skin vibration detectible at the vibration sensor.

17. The method of claim 16, wherein measuring skin vibrations characterizing the set of muscle twitches comprises measuring at least at one of an accelerometer and an audio sensor configured to detect skin vibrations of the patient.

18. The method of claim 16, wherein automatically modulating the stimulus parameter of the first set of stimulus parameters, based upon the comparison, comprises automatically increasing an intensity of the TENS treatment if a parameter derived from the muscle twitch amplitude is below the threshold.

19. The method of claim 16, further comprising entering a calibration state, configured to calibrate transmission of the TENS treatment, based upon a response from the patient, wherein entering the calibration state comprises transmitting an initial TENS treatment to the patient, characterized by an initial set of TENS treatment parameters, and adjusting at least a subset of the initial set of TENS treatment parameters, until the response from the patient satisfies a calibration threshold.

20. A system for managing pain, configured to be worn by a patient, wherein the system includes a housing that interfaces with the body of the patient, the system comprising:
an electrode array, coupled to the housing, comprising a first electrode and a second electrode for providing a TENS treatment to the patient;
a muscle twitch sensor subsystem, coupled to at least one of the housing and the electrode array, that includes a vibration sensor configured to measure skin vibrations characterizing a set of muscle twitches from the patient that are induced by the electrode array, thereby yielding a measured muscle twitch signal characterized by a set of measured muscle twitch values;
an electronics subsystem, coupled to the housing, comprising a power module configured to power the system, a pulse generator coupled to the electrode array and configured to transmit the TENS treatment to the patient, and a control module configured to receive the measured muscle twitch signal; wherein the electronics subsystem is configured to automatically modulate a parameter of the TENS treatment based upon the set of measured muscle twitch values until a threshold is satisfied, thereby managing pain of the patient; and
a connector configured to couple at least one of the first electrode and the second electrode to the electronics subsystem.

* * * * *